United States Patent [19]

Cragg

[11] Patent Number: 4,772,264

[45] Date of Patent: Sep. 20, 1988

[54] CATHETER INTRODUCTION SET

[75] Inventor: Andrew H. Cragg, St. Paul, Minn.

[73] Assignee: Regents of the University of Minnesota, Minneapolis, Minn.

[21] Appl. No.: 877,320

[22] Filed: Jun. 23, 1986

[51] Int. Cl.$^4$ .............................................. A61M 5/00
[52] U.S. Cl. .................................. 604/158; 604/165; 604/168; 604/179
[58] Field of Search ...................... 604/164, 158–163, 604/174, 171, 179; 128/658, 772

[56] References Cited

U.S. PATENT DOCUMENTS

| | | | |
|---|---|---|---|
| 2,008,340 | 7/1935 | Salvati et al. ........................ | 604/174 |
| 3,262,448 | 7/1966 | Ring et al. . | |
| 3,714,945 | 2/1973 | Stanley ................................ | 604/164 |
| 4,006,743 | 2/1977 | Kowarski ........................ | 604/158 X |
| 4,037,600 | 7/1977 | Poncy et al. . | |
| 4,068,659 | 1/1978 | Moorehead . | |
| 4,068,660 | 1/1978 | Beck . | |
| 4,324,237 | 4/1982 | Buttaravoli . | |
| 4,525,157 | 6/1985 | Vaillancourt ........................ | 604/165 |

Primary Examiner—Stephen C. Pellegrino
Attorney, Agent, or Firm—Kinney & Lange

[57] ABSTRACT

A catheter introduction set for introducing a catheter tube into blood vessels such as veins and arteries, includes a hollow needle, a catheter tube surrounding a flexible safety guide tube extending through the needle passageway. The guide tube is initially retracted. The needle will be inserted into a vein or artery and the guide tube provides an immediate feedback of blood at its remote end, thus indicating the needle is inside a blood vessel. After the needle has pierced the blood vessel, the safety guide tube is advanced into the lumen of the blood vessel to provide a guide for sliding the catheter tube into the pierced vessel and permitting retraction of the needle. The capillary tube requires little blood pressure to provide the blood feedback indicating that a vessel has been pierced, which makes the unit suitable use in for small veins, as well as arteries. When the catheter tube has been guided into the vessel, the needle and the guide tube are withdrawn, leaving the catheter tube in place. The end connector on the catheter tube has a clip for adhesive tape to be applied to the skin for quickly and easily holding the catheter tube in position.

4 Claims, 1 Drawing Sheet

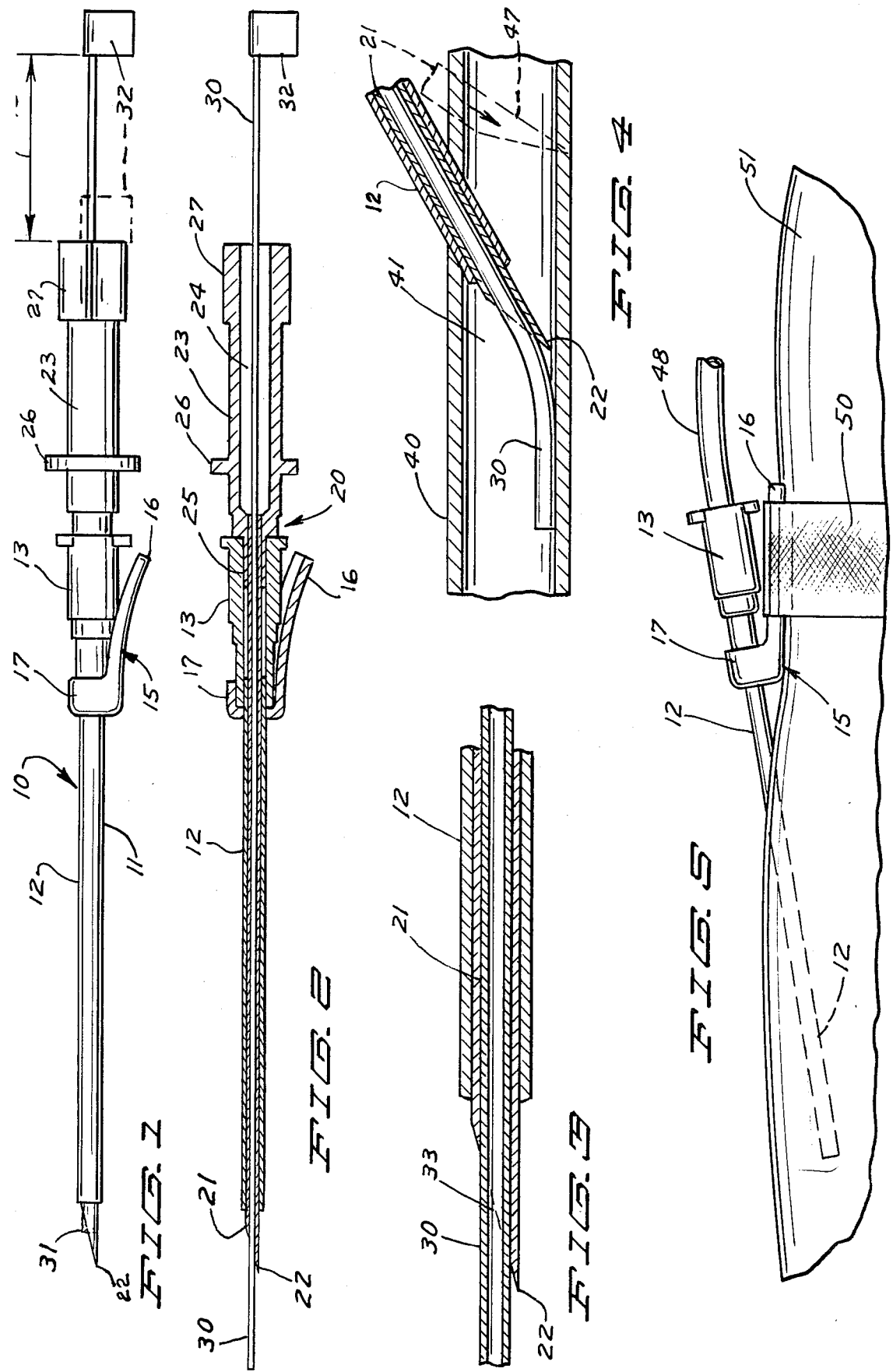

CATHETER INTRODUCTION SET

BACKGROUND OF THE INVENTION

1. Field of the Invention

The present invention relates to a catheter introduction set which provides reliable and safe introduction of catheters into blood vessels.

2. Description of the Prior Art

U.S. Pat. No. 4,417,886 discloses a catheter introduction set comprising a kit with a small, flexible wire guide on the interior of the introduction needle. The wire is used for guiding a catheter surrounding the introduction needle in place as the introduction needle is withdrawn from the blood vessel. The guide wire is solid and has to be withdrawn completely from the needle interior when the needle is first introduced into a vessel to permit blood to surge back into a sight chamber or into a tube that is attached to the introduction set. After the feedback of blood the wire is then moved through the needle into the lumen of the blood vessel. The catheter is slid along the guide into the vessel and the needle is withdrawn while leaving the catheter tube in place in the blood vessel. The guide wire also has to be long enough to be withdrawn from the needle and then rethreaded through the needle after the needle has been introduced into the blood vessel. An extra long guide tube is necessary for preventing contamination of the guide wire as the wire is withdrawn during the initial introduction of the needle to permit blood to flow out of the needle for an indication that a blood vessel has been pierced. This elongates a system substantially and causes extra cost in making and packaging, and also increases the difficulty of use.

U.S. Pat. No. 4,068,660 also shows a catheter placement assembly improvement utilizing a hollow spring on the interior of a catheter tube or plastic cannula, which catheter in turn is on the interior of the needle used for insertion into a blood vessel. This arrangement requires a needle that is larger diameter than the catheter end, and is otherwise somewhat similar to the unit shown in U.S. Pat. No. 4,417,886.

U.S. Pat. No. 3,903,885 also shows a device for introducing flexible catheters having a center stiffening mandrel 13 that is placed on the interior of the catheter.

U.S. Pat. No. 4,068,659 shows a catheter placement assembly which also uses an interior plastic cannula that is on the inside of the needle, and which is slid through the needle into a blood vessel once the needle has penetrated the wall of the blood vessel. Here, too, a large size needle is necessary in order to have a full size catheter, and it is necessary that the assembly be elongated to accommodate the need for maintaining the exposed portions sterile.

U.S. Pat. No. 3,262,448 shows an intervenious catheter placement set with a catheter positioned on the interior of a needle.

U.S. Pat. No. 4,037,660 also illustrates a catheter set with a catheter introduced into the side of the needle and adapted to be threaded into the blood vessel after the needle has been placed therein.

Various devices have been also made for holding catheters and the associated tubing in place. U.S. Pat. No. 4,324,237 shows such a device having a complex securement and dressing device providing a window over the puncture or wound site.

SUMMARY OF THE INVENTION

The present invention relates to a catheter introduction set using a flexible catheter tube, which surrounds an introduction needle and which includes an interior capillary (small diameter) safety guide tube on the interior of the needle. The guide tube can be slid along the needle for introduction into a blood vessel. The guide tube is very small size, is flexible and provides a blood passageway for an indication of needle penetration of a blood vessel as soon as penetration occurs. The flexible guide tubing thus acts as an indicator, and when slid past the point of the needle into the lumen of the blood vessel also acts as a reliable guide for the flexible catheter tube.

Immediate indication of needle penetration of the vessel is obtained (which saves times), and even in situations where the needle tip is partially penetrating an opposite side wall of the blood vessel from the point of needle entry, the guide tube of the present invention will still provide a passage for a small blood flow reliably indicating that penetration of the blood vessel has in fact been made. Then it is known that even if resistance to catheter entry is encountered, the vessel has been penetrated and by slight manipulation the catheter can be moved into the lumen of the blood vessel without need for removing the needle and reinserting it.

The introduction set of the present invention is also relatively inexpensive to make, and conserves length because the guide tube does not have to be retracted out of the needle to obtain the indictor of blood vessel penetration. The parts of the system that are on the exterior of the needle when the device is removed from its sterile packaging do not enter the body, thus elaborate measures to avoid contamination of exposed parts are not necessary.

The catheter set further includes a clip for quickly fastening the catheter in place once it has been properly guided into a blood vessel. The small clip can be molded directly to a needed external tubing connector for the catheter.

BRIEF DESCRIPTION OF THE DRAWINGS

FIG. 1 is a side view of a catheter introduction set made according to the present invention;

FIG. 2 is a sectional view of the device in FIG. 1 taken along the longitudinal axis thereof;

FIG. 3 is an enlarged sectional view of the needle tip of the introduction set showing a safety guide tube made according to the present invention on the interior thereof and also showing the external surrounding catheter;

FIG. 4 is a sectional view of a typical blood vessel showing the safety tube being partially inserted, with the needle and catheter penetrating a wall of the blood vessel; and FIG. 5 is a side view of a catheter inserted in place showing a fastening clip in use.

DETAILED DESCRIPTION OF THE PREFERRED EMBODIMENTS

A device or set for introducing a flexible catheter is shown in initial assembly generally at 10, and includes a catheter assembly 11 that has a conventional catheter tube section 12, which will be inserted into a blood vessel. A female luter-type fitting 13 is formed at the rear of the catheter tube 12. The catheter tube 12 and fitting 13 are conventional. The catheter tube 12 is mounted at one end of the interior of the female fitting 13 in a conventional manner. The fitting 13 has a retaining clip 15 mounted at one end thereof, which comprises a retaining finger 16 held on a hub 17. The finger 16 is spaced from the main portion of the female fitting 13. Hub 17 is attached to the end of the fitting 13 where the catheter tube 12 extends outwardly.

An introduction needle assembly indicated generally at 20 includes a hollow needle 21 that has a sharpened point or end 22. The needle 21 is a cannula needle having an interior passageway. The needle 21 is fixed to and extends from a needle hub 23 forming part of the needle assembly 20. Hub 23 has a neck portion 25 where the needle 21 is attached and has a larger diameter interior chamber 24, as shown, opening to the exterior. The neck 25 has a reduced outer diameter which will friction fit into the interior opening of the female connector 13 and the needle is in place within the fitting 13 in the initial assembly. The hub 23 has an external grip ring 26 thereon, and an end portion 27 that can be used for gripping and/or for attaching other members as desired. The neck 25 can be removed from connector 13 manually with little effort. The hub 23 and connector 13 do, however, remain assembled unless manually moved apart.

The needle 21 is suitably fixed held in the neck 25. As can be seen, the needle 21 is of size to slidably fit inside the catheter tube 12 and extends, when the neck 25 is positioned in the fitting 13, to be slightly longer than the catheter tube 12 (which is very flexible) so that the point 22 protrudes from the catheter tube.

A flexible, small diameter safety tube indicated at 30 is inserted through the interior passage of the needle 21, and in initial assembly is placed so that it is just slightly to the interior of the needle 21 from the point 22, generally as shown at 31 in FIG. 1. A flag or gripping tab 32 is provided at the opposite end of the tube 30. The tube 30 can be made of teflon. The tubing for tube 30 is commercially available, and forms a capillary tube. As shown in FIG. 3, the safety guide tube 30 has an interior passageway 32 (the scale is greatly enlarged in FIG. 3), and the outer surface of the tube 30 fits quite closely on the interior surface of the passageway or cannula of the needle 21. This prevents any substantial leakage of blood between the inner surface of the needle 21 and the outer surface of the safety guide tube 30. Also as seen in FIG. 3, the catheter tube 12 fits snuggly over the needle 21.

The safety guide tube 30 is retracted as in the position shown in FIG. 1 when the needle is first inserted into a blood vessel, which is shown generally at 40 in FIG. 4. In proper position, as shown in solid lines in FIG. 4, the needle point 22 will be used to penetrate the wall of the blood vessel and will pass into the lumen 41 of the blood vessel. The opening to the cannula of the needle 21 then will be in the lumen of the blood vessel. This also causes the catheter tube 12 to penetrate through the blood vessel wall as shown in FIG. 4. As soon as the tip 22 penetrates the vessel sufficiently to expose the opening or orifice of the cannula and tube 30, blood will be fed back through the chamber or passageway 33 in the safety guide tube 30 to the outer end of the tube 30 near the tab or flag 32. Penetrating a vessel with the needle will be immediately apparent to the user.

It is important to note that in the packaging, the initial exposed length of the safety guide tube 30 from member 27 to flag 32 needs to be only as long as that length which is required for acting as a guide for the catheter as the catheter is moved further into the lumen and the needle is withdrawn. Generally speaking, a protrusion of the safety guide tube 30, when the tab or flag 32 is in its dotted line position against the member 27, of about 5-6 cm. has been found to be satisfactory. Thus, dimension 45 (FIG. 1) can be 5-6 cm.

The overall length of the tube 30 can be minimized so that when the introduction set is in its position shown in FIG. 1, the protrusion length indicated by the dimension 45 is substantially less than the length of the needle 21 (from neck 25 of hub 23 to the outer tip of the needle), so that there is no fear of contaminating the tube 30 that will penetrate into the blood vessel. In other words, the portion of the safety guide tube 30 that is within the needle 21 is shielded from contamination even after the packaging is open. No portion of the tube 30 which is exposed to the atmosphere will enter the blood vessel. The tube 30 can be inserted until flag 32 strikes the end of member 27 without fear of infecting the patient even without special protection measures after opening the outer package for the catheter set. As was stated, a protrusion of 5-6 cm. as indicated by dimension 45 is adequate, if 5-6 cm. of safety guide tube 30 within the blood vessel is adequate for guiding the catheter tube 12 into the blood vessel, and the needle length may be in the range of 8 cm. so the exposed portion of the tube 30 never enters the blood vessel.

If desired, a chamber of slightly larger diameter than tube 30 can be provided at the outer end of the safety guide tube 30 where the flag or tab 32 is attached, to provide a reservoir for blood flow, but in general, the loss of blood from the safety guide tube 30 is quite low (a drip is all that is present) because the internal diameter of passageway 33 of tube 30 is kept very small. The end of tube 30 may have a cap, cover or clip to shut off flow when desired.

An advantage of utilizing a tubular, flexible member such as the safety guide tube 30 is illustrated in the dotted line showing of the needle in FIG. 4. If the point of the needle 22 partially penetrates the far wall of a blood vessel as indicated at 47, with an ordinary music wire guide on the interior of the needle, there is no indication that the needle is in a blood vessel or has actually penetrated the blood vessel because there will be no reverse blood flow through the solid wire.

On the other hand, with the present invention even though the needle cannot be moved in this position because the needle point 22 is snagged or embedded into the far wall of the blood vessel, the passageway 33 of the safety guide tube 30 is open to the lumen of the blood vessel and blood will appear at the far end of tube 30. The attendant has a positive indication that the vein or blood vessel has in fact been penetrated. The attendant knows that slight withdrawal or some movement of the needle, or even a slight extra force will permit the catheter to be slid off so it can be inserted into the blood vessel. The solid line showing of the needle in FIG. 4 illustrates how and where the tube 30 will act as a guide within the lumen. Note that in the dotted line position shown in FIG. 4, with the end of the needle partially penetrating the far wall of the blood vessel, and the needle almost perpendicular to the axis of the blood vessel, the safety guide tube 30 cannot easily make the bend out of the needle into the lumen of the blood vessel. With an ordinary music wire guide, no indication is present that the blood vessel has been penetrated and a complete new insertion would be required.

Once the safety guide tube 30 has been slid so that it is extended into the blood vessel, the catheter is then slid into place along the safety guide tube 30. The connector 13 is slid off the hub 23 and moved along the exterior of the needle until it is fully inserted. The catheter tube 12 will slide along the guide end of safety guide tube 30 and may actually extend into the blood vessel beyond the inner end of tube 30. The needle 21 and the safety guide tube 30 are withdrawn by pulling on the member 27 while holding connector 13 from reverse movement. As soon as the needle 21 and safety guide tube 30 are removed from the catheter, a suitable tube indicated at 48 is inserted into the connector 13 in a normal manner for catheter use. The safety guide tube 30 will be pulled out of the catheter with the needle because the flag 32 will be in its dotted line position and will be carried out as the needle is withdrawn.

Because the safety guide tube 30 is inserted further into the blood vessel that the needle, the needle is backed out until the protruding end of safety guide tube 30 is free of connector 13.

As shown in FIG. 5, the finger 16 can be held in place on the skin of a patient with a single piece of adhesive tape 50 adhering to the arm or other body portion 51, to hold the catheter tube 12 and connector 13 positively in place easily. No special adapters are needed and there is no need to wrap adhesive tape around the entire connector 13. The small finger 16, which is spaced from the wall of connector 13, provides a convenient gap for inserting a single piece of tape for holding the catheter assembly positively in place when it is being used.

The insertion is greatly simplified, as stated with the present device, and cost is kept low. The tube 30 can be reinforced with an imbedded plastic or wire if desired for increasing the rigidity. The tube 30 must be non-toxic, of course. Even in small blood vessels and in veins the indication of penetration will be immediately apparent.

What is claimed is:

1. A catheter introduction set for the introduction of a catheter tube into a blood vessel comprising:
    a flexible catheter assembly having a catheter tube and having a connector at one end of the tube, said connector having an input end;
    a hollow needle having a base end and a point and being slidably, removably fitted on the interior of said catheter tube, and having tubular hub means at its base end for holding the needle and catheter in an assembly, said needle having an interior, longitudinally extending passageway; and
    a flexible tube slidably mounted on the interior passageway of the needle, said flexible tube having a second small diameter passageway therein, said flexible tube having a first end portion extending outwardly from the base end of the needle and a short distance outwardly of an outer end of the hub means when the opposite end of the flexible tube is adjacent the point of the needle, whereby upon any penetration of the needle into a blood vessel an immediate feedback of blood is present in the flexible tube to provide a positive indication of blood vessel penetration, the flexible tube being slidable through the needle passageway into the interior of a blood vessel that is penetrated by the needle point, whereby the second passageway provides a passageway for blood flow directly from such blood vessel to the exterior, and wherein the flexible tube has sufficient length to permit it to be inserted to extend past the needle point into the interior of such blood vessel to provide a guide for the catheter tube that is mounted over the needle as the catheter tube is then slid over the needle and past the needle point into the blood vessel, the flexible tube having means thereon at the outer end for removal from the catheter tube and connector when the needle is removed from the connector.

2. The apparatus as specified in claim 1 and a retainer finger mounted on said catheter assembly and having a finger portion generally parallel to a longitudinal axis of the catheter tube so that a piece of adhesive tape may be placed over the finger and the catheter assembly for holding the catheter tube and connector in place on a patient.

3. The apparatus as specified in claim 1 wherein said flexible tube closely fits the interior passageway of said needle to substantially prevent blood from flowing between the interior surface of the needle and the exterior surface of said flexible tube.

4. The apparatus as specified in claim 1 wherein said hub means for coupling the needle to the connector comprises a hub having a center passageway and a neck having an outer surface that frictionally fits into the connector of said catheter, said hub being manually separable from the connector to permit the catheter tube of the catheter assembly to be inserted into the lumen of a blood vessel penetrated by the needle as the needle remains in position, and when the catheter tube is in place to permit removing the needle the flexible tube from such blood vessel.

* * * * *

UNITED STATES PATENT AND TRADEMARK OFFICE
CERTIFICATE OF CORRECTION

PATENT NO. : 4,772,264

DATED : September 20, 1988

INVENTOR(S) : Andrew H. Cragg

It is certified that error appears in the above-identified patent and that said Letters Patent is hereby corrected as shown below:

Column 6, line 48, after "needle", delete "the" and insert --and--.

Signed and Sealed this

Seventh Day of February, 1989

Attest:

DONALD J. QUIGG

Attesting Officer

Commissioner of Patents and Trademarks